(12) United States Patent
Glazer (10) Patent No.: US 7,279,463 B2
(45) Date of Patent: Oct. 9, 2007

(54) TRIPLE-HELIX FORMING OLIGONUCLEOTIDES FOR TARGETED MUTAGENESIS

(75) Inventor: Peter M. Glazer, Guilford, CT (US)

(73) Assignee: Yale University, New Haven, CT (US)

( * ) Notice: Subject to any disclaimer, the term of this patent is extended or adjusted under 35 U.S.C. 154(b) by 1017 days.

(21) Appl. No.: 09/978,333

(22) Filed: Oct. 15, 2001

(65) Prior Publication Data
US 2003/0232768 A1 Dec. 18, 2003

Related U.S. Application Data

(60) Continuation-in-part of application No. 09/411,291, filed on Oct. 4, 1999, now Pat. No. 6,303,376, which is a division of application No. 08/476,712, filed on Jun. 7, 1995, now Pat. No. 5,962,426.

(51) Int. Cl.
A61K 31/7088 (2006.01)
A61K 31/713 (2006.01)
C07H 21/02 (2006.01)
C07H 21/04 (2006.01)

(52) U.S. Cl. ............................ 514/44; 514/45; 514/49; 435/440; 435/441; 435/455; 435/471; 536/23.1; 536/24.5

(58) Field of Classification Search .................. 514/44; 536/23.1, 24.5; 435/5, 6, 440, 441, 455
See application file for complete search history.

(56) References Cited

U.S. PATENT DOCUMENTS 5,422,251 A 6/1995 Fresco
5,776,744 A * 7/1998 Glazer et al. ............... 435/463
5,962,426 A 10/1999 Glazer

FOREIGN PATENT DOCUMENTS

WO     WO95/01364     1/1995

OTHER PUBLICATIONS

Barre et al. PNAS. Mar. 28, 2000. 97(7): 3084-3088.*
Seidman et al. The Journal of Clinical Investigation. Aug. 2003. 112(4): 487-494.*
Baumann, et al., "Role of the human RAD51 protein in homologous recombination and double-stranded-break repair," *Trends Biochem Sci* 23(7):247-251 (1998).
Beal, et al., "Second structural motif for recognition of DNA by oligonucleotide-directed triple-helix formation,"*Science* 251:1360-1363 (1991).
Beal, et al., "The influence of single base triplet changes on the stability of Pur-Pur-Pyr triple helix determined by affinity cleaving," *Nuc. Acids Res.* 20(11):2773-2776 (1992).
Blume, et al., "Triple helix formation by purine-rich oligonucleotides targeted to the human dihydrofolate reductase promoter," *Nucleic Acids Res.* 20:1777-1784 (1992).
Brenneman, et al., "Stimulation of intrachromosomal homologous recombination in human cells by electroporation with site-specific endonucleases," *Proc. Natl. Acad. Sci.* USA 93(8): 3608-12 (1996).
Campbell, et al., "Homologous recombination involving small single-stranded oligonucleotides in human cells," New Biol. 1(2):223-7 (1989).
Capecchi, "Altering the genome by homologous recombination," *Science* 244(4910): 1288-1292 (1989).
Chan, et al., "Targeted correction of an episomal gene in mammalian cells by a short DNA fragment tethered to a triplex-forming oligonucleotide," J. Biol. Chem. 274(17): 11541-11548 (1999).
Cooney, et al., "Site-specific oligonucleotide binding represses transcription of the human c-myc gene in vitro," *Science* 241: 456-459 (1988).
Durland, et al., "Binding of triple helix forming oligonucleotides to sites in gene promoters," *Biochemistry* 30:9246-9255 (1991).
Duval-Valentin, et al., "Specific inhibition of transcription by triple helix-forming oligonucleotides," *Proc. Natl. Acad. Sci. USA* 89:504-508 (1992).
Faruqi, et al., "Triple-helix formation induces recombination in mammalian cells via a nucleotide excision repair-dependent pathway," *Mol Cell Biol* 20(3): 990-1000 (2000).
Felsenfeld, et al., "Formation of a three-stranded polynucleotide molecule," *J. Am. Chem. Soc.* 79:2023-2024 (1957).
Francois, et al., "Sequence-specific recognition and cleavage of duplex DNA via triple-helix formation by oligonucleotides covalently linked to a phenanthroline-copper chelate," *Proc. Natl. Acad. Sci. USA* 86:9702-9706 (1989).

(Continued)

*Primary Examiner*—Carla J. Myers
(74) *Attorney, Agent, or Firm*—Pabst Patent Group LLP (57) ABSTRACT

A high affinity, triplex-forming oligonucleotide and methods for use thereof wherein an oligonucleotide is used to form a triple-stranded nucleic acid molecule with a specific DNA segment of a target DNA molecule. Upon formation of the triplex, the binding of the oligonucleotide stimulates mutagenesis within or adjacent to the target sequence using cellular DNA synthesis or repair mechanisms thereby producing heritable changes in a human or animal. The mutation activates, inactivates or alters the activity and function of the target molecule. This mutation may be the result of a recombinagenic mechanism induced by the oligonucleotide.

10 Claims, 2 Drawing Sheets

OTHER PUBLICATIONS

Glazer, et al., "DNA mismatch repair detected in human cell extracts," *Mol. Cell. Biol.* 7:218-224 (1987).

Goncz, et al., "Site-directed alteration of genomic DNA by small-fragment homologous replacement," *Methods Mol. Biol.* 133:85-89 (2000).

Grigoriev, et al., "A triple helix-forming oligonucleotide-intercalator conjugate acts as a transcriptional repressor via inhibition of NF kappa B binding to interleukin-2 receptor alpha-regulatory sequence," *J. of Biological Chem.* 267:3389-3395 (1992).

Hanson, et al., "Analysis of biological selections for high-efficiency gene targeting," *Mol. Cell. Biol.* 15(1):45-51 (1995).

Havre, et al., "Targeted mutagenesis of simian virus 40 DNA mediated by a triple helix-forming oligonucleotide," *J. Virology* 67:7324-7331 (1993).

Helene, "Sequence-selective recognition and cleavage of double-helical DNA," *Curr. Opinion Biotechnology* 4:29-36 (1993).

Ito, et al., "Sequence-specific DNA purification by triplex affinity capture," *Proc. Natl. Acad. Sci. USA* 89:495-498 (1992).

Jakubczak, et al., "Analysis of genetic instability during mammary tumor progression using a novel selection-based assay for in vivo mutations in a bacteriophage lambda transgene target," *Proc. Natl. Acad. Sci. USA* 93:9073-9078 (1996).

Jones, et al., "Preferential binding of the xeroderma pigmentosum group A complementing protein to damaged DNA," *Biochemistry* 32:12096-12104 (1993).

Letai, et al., "Specificity in formation of triple-stranded nucleic acid helical complexes: studies with agarose-linked polyribonucleotide affinity columns," *Biochemistry* 27:9108-9112.

Lin, et al., "Extrachromosomal recombination in mammalian cells as studied with single- and double-stranded DNA substrates," *Mol. Cell Biol* 7(1):129-140 (1987).

Lin, et al., "Use of EDTA derivatization to characterize interactions between oligodeoxyribonucleoside methylphomates and nucleic acids," *Biochemistry* 28:1054-1061 (1989).

Luo, et al., "High-frequency intrachromosomal gene conversion induced by triplex-forming oligonucleotides microinjected into mouse cells," *Proc. Natl. Acad. Sci. USA* 97(16): 9003-9008 (2000).

Maher, et al., "Analysis of promoter-specific repression by triple-helical DNA complexes in a eukaryotic cell-free transcription system," *Biochemistry* 31:70-81 (1992).

Maher, et al., "Inhibition of DNA binding proteins by oligonucleotide-directed triple helix formation," *Science* 245:725-730 (1989).

Mergny, et al., "Sequence specificity in triple-helix formation: experimental and theoretical studies of the effect of mismatches on triplex stability," *Biochemistry* 30:9791-9798 (1991).

Moser, et al., "Sequence-specific cleavage of double helical DNA by triple helix formation," *Science* 238:645-650 (1987).

Myhr, "Validation studies with Muta Mouse: a transgenic mouse model for detecting mutations in vivo," *Environ. Mol. Mutagen* 18:308-315(1991).

Narayanan, et al., "Elevated levels of mutation in multiple tissues of mice deficient in the DNA mismatch repair gene Pms2," *Proc. Natl. Acad. Sci. USA* 94:3122-3127 (1997).

Orson, et al., "Oligonucleotide inhibition of IL2R alpha mRNA transcription by promoter region collinear triplex formation in lymphocytes," *Nucleic Acids Res.* 19:3435-3441 (1991).

Park, et al., "Formation of a ternary complex by human XPA, ERCC1, and ERCC4(XPF) excision repair proteins," *Proc. Natl. Acad. Sci. USA* 91:5017-5021 (1994).

Parris, et al., "Proximal and distal effects of sequence context on ultraviolet mutational hotspots in a shuttle vector replicated in xeroderma cells," *J Mol Biol.* 236:491-502 (1994).

Pei, et al., "Site-specific cleavage of duplex DNA by a semisynthetic nuclease via triple-helix formation," *Proc. Natl. Acad. Sci. USA* 87:9858-9862 (1990).

Perroualt, et al., "Sequence-specific artificial photo-induced ndonucleases based on triple helix-forming oligonucleotides," *Nature* 344:358-360 (1990).

Postel, et al., "Evidence that a triplex-forming oligodeoxyribonucleotide binds to the c-myc promoter in HeLa cells, thereby reducing c-myc mRNA levels," *Proc. Natl. Acad. Sci. USA* 88:8227-8231 (1991).

Posvic, et al., "Sequence-Specific Alkylation of Double-Helix DNA by Oligonucleotide-Directed Triple-Helix Formation," *J. Am. Chem Soc.* 112:9428-9430 (1990).

Praseuth, et al., "Sequence-specific binding and photocrosslinking of alpha and beta oligodeoxynucleotides to the major groove of DNA via triple-helix formation," *Proc. Natl. Acad. Sci. USA* 85:1349-1353 (1988).

Reardon, et al., "Removal of psoralen monoadducts and crosslinks by human cell free extracts," *Nucleic Acids Res.* 19:4623-4629 (1991).

Sambrook, et al., Molecular Cloning: A Laboratory Manual, second edition, Cold Spring Harbor Laboratory Press, New York (1990).

Sancar, "DNA excision repair," *Annu. Rev. Biochem.* 65:43-81 (1996).

Shivji, et al., "Proliferating cell nuclear antigen is required for DNA excision repair," *Cell* 69: 367-374 (1992).

Sibghat-Ullah, et al., "Human nucleotide excision repair in vitro: repair of pyrimidine dimers, psoralen and cisplatin adducts by HeLa cell-free extract," *Nucleic Acids Res.* 17:4471-4484 (1989).

Strobel, et al., "Site-specific cleavage of human chromosome 4 mediated by triple-helix formation," *Science* 254:1639-1642 (1991).

Sung, et al., "Recombination factors of *Saccharomyces cerevisiae*," *Mutat Res* 451:257-75 (2000).

Takasugi, et al., "Sequence-specific photo-induced cross-linking of the two strands of double-helical DNA by a psoralen covalently linked to a triple helix-forming oligonucleotide," *Proc. Natl. Acad. Sci. USA* 88:5602-5606 (1991).

Thacker, "A surfeit of RAD51-like genes?," *Trends Genet* 15(5):166-8 (1999).

Vasquez, et al., "Chromosomal mutations induced by triple-forming oligonucleotides in mammalian cells," *Nucleic Acids Res.* 27:1176-1181 (1999).

Wang, et al., "Mutagenesis in mammalian cells induced by triple helix formation and transcription-coupled repair," *Science* 271: 802-805 (1996).

Wang, et al., "Targeted mutagenesis in mammalian cells mediated by intracellular triple helix formation," *Mol. Cell. Biol.* 15:1759-1768 (1995).

Wood, et al., "Complementation of the xeroderma pigmentosum DNA repair defect in cell-free extracts," *Cell* 53:97-106 (1988).

Young, et al., "Triple helix formation inhibits transcription elongation in vitro," *Proc. Natl. Acad. Sci. USA* 88:10023-10026 (1991).

* cited by examiner

FIG. 1

Multiple point mutations

```
                                                                         225 C>G
                                                                         199 C>T
                                                                         215 G>A
                                   A                              
                                   A                              
                                   G               A              
                      I                        C   A              
                      A           IA           C   A A            
3'                    G                   T       GA                                                                                    5'
CTTAAGCTCTCGGGACGAGCTCGACACCACCCCAAGGGCTCGCCGGTTTCCCTGTCTGAGATTAGACGGCAGTAGCTGAAGCTTCCAAGCTTAGGAAGGGGGGGTGGTGGGAGGGGGAG
       80        90        100       110       120       130       140       150       160       170       180
GAATTCGAGAGCCCTGCTCGAGCTGTGGTGGGTTCCCGAGCGGCCAAAGGGAGCAGACTCTAAATCTGCCGTCATCGACTTCGAAGGTTCGAATCCTTCCCCCCCACCACCCCCTCCCCCCTC
5' pre-tRNA (58-98)    Suppressor tRNA (99-183)                                Triplex binding site (Seq. ID No. 6)
```

Single point mutations

Deletions

TRIPLE-HELIX FORMING OLIGONUCLEOTIDES FOR TARGETED MUTAGENESIS

This application is a continuation-in-part of U.S. Ser. No. 09/411,291, filed on Oct. 4, 1999, now U.S. Pat. No. 6,303,376 which is a divisional of U.S. Ser. No. 08/476,712, filed on Jun. 7, 1995, which issued as U.S. Pat. No. 5,962,426 on Oct. 5, 1999.

The United States Government has certain rights in this invention by virtue of National Institutes of Health grant No. ES05775 to Peter M. Glazer.

This relates to the field of genetics, and more particularly relates to site-directed mutagenesis of a gene of interest.

BACKGROUND OF THE INVENTION

Since the initial observation of triple-stranded DNA many years ago by Felsenfeld et al., *J. Am. Chem. Soc.* 79:2023 (1957), oligonucleotide-directed triple helix formation has emerged as a valuable tool in molecular biology. Current knowledge suggests that oligonucleotides can bind as third strands of DNA in a sequence specific manner in the major groove in polypurine/polypyrimidine stretches in duplex DNA. In one motif, a polypyrimidine oligonucleotide binds in a direction parallel to the purine strand in the duplex, as described by Moser and Dervan, *Science* 238:645 (1987), Praseuth et al., *Proc. Natl. Acad. Sci. USA* 85:1349 (1988), and Mergny et al., *Biochemistry* 30:9791 (1991). In the alternate purine motif, a polypurine strand binds anti-parallel to the purine strand, as described by Beal and Dervan, *Science* 251:1360 (1991). The specificity of triplex formation arises from base triplets (AAT and GGC in the purine motif) formed by hydrogen bonding; mismatches destabilize the triple helix, as described by Mergny et al., *Biochemistry* 30:9791 (1991) and Beal and Dervan, *Nuc. Acids Res.* 11:2773 (1992).

Triplex forming oligonucleotides (TFOs) have been found useful for several molecular biology techniques. For example, triplex forming oligonucleotides designed to bind to sites in gene promoters have been used to block DNA binding proteins and to block transcription both in vitro and in vivo. (Maher et al., *Science* 245:725 (1989), Orson et al., *Nucleic Acids Res.* 19:3435 (1991), Postal et al., *Proc. Natl. Acad. Sci. USA* 88:8227 (1991), Cooney et al., *Science* 241:456 (1988), Young et al., *Proc. Natl. Acad. Sci. USA* 88:10023 (1991), Maher et al., *Biochemistry* 31:70 (1992), Duval-Valentin et al., Proc. Natl. Acad. Sci. USA 89:504 (1992), Blume et al., *Nucleic Acids Res.* 20:1777 (1992), Durland et al., *Biochemistry* 30:9246 (1991), Grigoriev et al., *J. of Biological Chem.* 267:3389 (1992), and Takasugi et al., *Proc. Natl. Acad. Sci. USA* 88:5602 (1991)). Site specific cleavage of DNA has been achieved by using triplex forming oligonucleotides linked to reactive moieties such as EDTA-Fe(II) or by using triplex forming oligonucleotides in conjunction with DNA modifying enzymes (Perrouault et al., *Nature* 344:358 (1990), Francois et al., *Proc. Natl. Acad. Sci. USA* 86:9702 (1989), Lin et al., *Biochemistry* 28:1054 (1989), Pei et al., *Proc. Natl. Acad. Sci. USA* 87:9858 (1990), Strobel et al., *Science* 254:1639 (1991), and Posvic and Dervan, *J. Am. Chem Soc.* 112:9428 (1992)). Sequence specific DNA purification using triplex affinity capture has also been demonstrated. (Ito et al., *Proc. Natl. Acad. Sci. USA* 89:495 (1992)). Triplex forming oligonucleotides linked to intercalating agents such as acridine, or to cross-linking agents, such as p-azidophenacyl and psoralen, have been utilized, but only to enhance the stability of triplex binding. (Praseuth et al., *Proc. Natl. Acad. Sci. USA* 85:1349 (1988), Grigoriev et al., *J. of Biological Chem.* 267:3389 (1992), Takasugi et al., *Proc. Natl. Acad. Sci. USA* 88:5602 (1991).

Gene therapy can be defined by the methods used to introduce heterologous DNA into a host cell or by the methods used to alter the expression of endogenous genes within a cell. As such, gene therapy methods can be used to alter the phenotype and/or genotype of a cell.

Targeted modification of the genome by gene replacement is of value as a research tool and in gene therapy. However, while facile methods exist to introduce new genes into mammalian cells, the frequency of homologous integration is limited (Hanson et al., (1995) Mol. Cell. Biol. 15(1), 45-51), and isolation of cells with site-specific gene insertion typically requires a selection procedure (Capecchi, M. R., (1989) Science 244(4910), 1288-1292). Site-specific DNA damage in the form of double-strand breaks produced by rare cutting endonucleases can promote homologous recombination at chromosomal loci in several cell systems, but this approach requires the prior insertion of the recognition sequence into the locus.

Methods which alter the genotype of a cell typically rely on the introduction into the cell of an entire replacement copy of a defective gene, a heterologous gene, or a small nucleic acid molecule such as an oligonucleotide, to treat human, animal and plant genetic disorders. The introduced gene or nucleic acid molecule, via genetic recombination, replaces the endogenous gene. This approach requires complex delivery systems to introduce the replacement gene into the cell, such as genetically engineered viruses, or viral vectors.

Alternatively, gene therapy methods can be used to alter the expression of an endogenous gene. One example of this type of method is the field of antisense therapy. In antisense therapy, a nucleic acid molecule is introduced into a cell, the nucleic acid molecule being of a specific nucleic acid sequence so as to hybridize or bind to the mRNA encoding a specific protein. The binding of the antisense molecule to an mRNA species decreases the efficiency and rate of translation of the mRNA.

Gene therapy is being used on an experimental basis to treat well known genetic disorders of humans such as retinoblastoma, cystic fibrosis, and sickle cell anemia. However, in vivo efficiency is low due to the limited number of recombination events actually resulting in replacement of the defective gene.

A method for targeted mutagenesis of a target DNA molecule would be useful as another means of gene therapy which can be carried out in vivo. Such a method would also be a useful research tool for genetic engineering or for studying genetic mechanisms such as DNA repair.

Therefore, it is an object of the present invention to provide a method for in vivo and in vitro targeted mutagenesis of a target DNA molecule.

It is a further object of the present invention to provide a method for in vivo and in vitro targeted recombination, wherein previous modification of the target is not required.

It is a further object of the present invention to use triplex forming oligonucleotides (TFOs) to promote and increase the frequency of recombination resulting in a targeted genetic change.

It is a further object of the present invention to use TFOs to promote targeted genetic changes in human and animal cells.

It is a further object of the present invention to provide a method for mutagenesis of a target DNA molecule that is highly specific and efficient.

It is a further object of the present invention to provide a method for treating genetic disorders by gene therapy without the need for a viral vector.

It is a further object of the present invention to provide a method for treating cancer.

It is a further object of the present invention to provide oligonucleotides for use in therapy and research.

TFOs are defined as triplex-forming oligonucleotides which bind as third strands to duplex DNA in a sequence specific manner.

SUMMARY OF THE INVENTION

High affinity, triplex-forming oligonucleotides and methods for use thereof are described herein. A high affinity oligonucleotide ($K_d \leq 2\times10^{-8}$) which forms a triple strand with a specific DNA segment of a target gene DNA is generated. It is preferable that the $K_d$ for the high affinity oligonucleotide is less than or equal to $2\times10^{-6}$. It is more preferable that the $K_d$ for the high affinity oligonucleotide is less than or equal to $2\times10^{-7}$. It is still more preferable that the the $K_d$ for the high affinity oligonucleotide be below $2\times10^{-8}$. It is still more preferable that the the $K_d$ for the high affinity oligonucleotide be below $2\times10^{-9}$ It is still more preferable that the the $K_d$ for the high affinity oligonucleotide be below $2\times10^{-10}$. The oligonucleotide binds/hybridizes to a target sequence within a target gene or target region of a chromosome, forming a triplex region. The binding of the oligonucleotide to the target region stimulates mutations within or adjacent to the target region using cellular DNA synthesis, recombination, and repair mechanisms. The mutation generated activates, inactivates, or alters the activity and function of the target gene.

If the target gene contains a mutation that is the cause of a genetic disorder, then the oligonucleotide is useful for mutagenic repair that restores the DNA sequence of the target gene to normal. If the target gene is a viral gene needed for viral survival or reproduction or an oncogene causing unregulated proliferation, such as in a cancer cell, then the mutagenic oligonucleotide is useful for causing a mutation that inactivates the gene to incapacitate or prevent reproduction of the virus or to terminate or reduce the uncontrolled proliferation of the cancer cell. The mutagenic oligonucleotide is also a useful anti-cancer agent for activating a repressor gene that has lost its ability to repress proliferation.

The triplex-forming oligonucleotide is also particularly useful as a molecular biology research tool to cause targeted mutagenesis. Targeted mutagenesis is useful for targeting a normal gene and for the study of mechanisms such as DNA repair. Targeted mutagenesis of a specific gene in an animal oocyte, such as a mouse oocyte, provides a useful and powerful tool for genetic engineering for research and therapy and for generation of new strains of "transmutated" animals and plants for research and agriculture. Investigation into the mechanism of triplex-induced recombination has also led to the formulation of materials and methods for use in inducing the targeted recombination of genetic sequences. A plasmid based system incorporating homologous fragments tethered to sequence specific TFOs, indicator bacteria, and a plasmid vector containing a mutated version of a reporter gene is used in conjunction with human cell extracts to promote targeted recombination.

The induction of targeted recombination may be best served, for example, to correct a mutation in a target gene that is the cause of a genetic disorder. Alternatively, if the target gene is a viral gene needed for viral survival or reproduction or an oncogene causing unregulated proliferation, such as in a cancer cell, then the use of recombinagenic TFOs may be usefull for inducing a mutation or correcting the mutation, by homologous recombination, thereby inactivating the gene to incapacitate or prevent reproduction of the virus or to terminate or reduce the uncontrolled proliferation of the cancer cell.

The binding of the oligonucleotide to the target region of a particular genetic sequence, can stimulate recombination in mammalian cells at a chromosomal locus containing two tandem copies of the herpes simplex virus thymidine kinase gene, following direct intranuclear microinjection of the oligonucleotides. (Luo, Z et al. (2000) Proc. Natl. Acad. Sci. USA 97(16), 9003-9008)).

Triplex-forming oligonucleotides are particularly useful as molecular research tools because they can be incorporated to specific target DNA sequences for mutagenesis. Targeted mutagenesis has been shown to be a very useful tool when employed to not only elucidate functions of genes and gene products, but alter known activities of genes and gene products as well.

DETAILED DESCRIPTION OF THE INVENTION

High affinity, triplex-forming oligonucleotides and methods of use in gene therapy, anti-viral therapeutics, scientific research, and genetic engineering of cells, animals and plants are provided. The oligonucleotides herein described bind with specificity to a chosen site in a target DNA molecule, forming a triplex region. The triplex acts to stimulate mutagenesis within or adjacent to the target region. The mutation activates, inactivates or alters the activity and function of a gene containing the target site.

The triplex-forming oligonucleotides herein described can further be used to stimulate homologous recombination of a separate DNA fragment into the target region. The oligonucleotide activates cellular DNA synthesis, recombination, and repair mechanisms through triple helix formation. The activated cellular mechanisms can be directed to recombine a second DNA fragment into the target region. The second DNA fragment may be tethered to the oligonucleotide or physically separate.

Oligonucleotides

The oligonucleotides herein described are synthetic or isolated nucleic acid molecules which selectively bind to or hybridize with a predetermined region of a double-stranded DNA molecule so as to form a triple-stranded structure. The predetermined region is referred to herein as the target sequence, target region, or target site.

Preferably, the target region of the double-stranded molecule contains or is adjacent to a defective or essential portion of a target gene, such as the site of a mutation causing a genetic defect, a site causing oncogene activation, or a site causing the inhibition or inactivation of an oncogene suppressor. Most preferably, the gene is a human gene.

Preferably, the oligonucleotide is a single-stranded nucleic acid molecule between 7 and 40 nucleotides in length, most preferably 10 to 20 nucleotides in length for in vitro mutagenesis and 20 to 30 nucleotides in length for in vivo mutagenesis. The base composition is preferably homopurine or homopyrimidine. Alternatively, the base composition is polypurine or polypyrimidine. However, other compositions are also useful.

The oligonucleotides herein described are preferably generated using known DNA synthesis procedures. In the Example that follows, the oligonucleotides were obtained from a commercial supplier.

The nucleotide sequence of the oligonucleotides herein described is selected based on the sequence of the target sequence, the physical constraints imposed by the need to achieve binding of the oligonucleotide within the major groove of the target region, and the need to have a low dissociation constant ($K_d$) for the oligonucleotide/target sequence. The oligonucleotides will have a base composition which is conducive to triple-helix formation and will be generated based on one of the known structural motifs for third strand binding. In the motif used in the Example which follows (the anti-parallel purine motif), a G is used when there is a GC pair and an A is used when there is a AT pair in the target sequence. When there is an inversion, a CG or TA pair, another residue is used, for example, a T is used for a TA pair. A review of base compositions for third strand binding oligonucleotides is provided in U.S. Pat. No. 5,422, 251.

Preferably, the oligonucleotide binds/hybridize to the target nucleic acid molecule under conditions of high stringency and specificity. Most preferably, the oligonucleotides bind in a sequence-specific manner within the major groove of duplex DNA. Reaction conditions for in vitro triple helix formation of an oligonucleotide probe or primer to a nucleic acid sequence vary from oligonucleotide to oligonucleotide, depending on factors such as oligonucleotide length, the number of G:C and A:T base pairs, and the composition of the buffer utilized in the hybridization reaction. An oligonucleotide substantially complementary, based on the third strand binding code, to the target region of the double-stranded nucleic acid molecule is preferred.

As used herein, an oligonucleotide is said to be substantially complementary to a target region when the oligonucleotide has a base composition which allows for the formation of a triple-helix with the target region. As such, an oligonucleotide is substantially complementary to a target region even when there are non-complementary bases present in the oligonucleotide. As stated above, there are a variety of structural motifs available which can be used to determine the nucleotide sequence of a substantially complementary oligonucleotide.

The triplex forming oligonucleotides (TFOs) used herein are also be designed to be tethered to a donor DNA fragment or used in conjunction to a non-tethered fragment that is homologous to the target sequence via a mixed sequence linker. This arrangement facilitates target site recognition via triple helix formation while at the same time positioning the tethered donor fragment for possible recombination and information transfer. This strategy is also intended to exploit the ability of a triplex, itself, to provoke DNA repair, potentially increasing the probability of recombination with the homologous donor DNA. It is understood in the art that the greater the number of homologous positions with the fragment will increase the probability that the fragment will be recombined into the target sequence, target region, or target site. The term "recombinagenic" as used herein, is used to define a DNA fragment, oligonucleotide, or composition as being able to recombine into a target site or sequence or induce recombination of another DNA fragment, oligonucleotide, or composition. Non-tethered, or unlinked fragments may range in length from 30 nucleotides to several thousand. It is to be understood that the oligonucleotide molecules, whether linked or unlinked, can exist in single stranded or double stranded form.

The preferred conditions under which a triple-stranded structure will form are standard assay conditions for in vitro mutagenesis and physiological conditions for in vivo mutagenesis. (See for example, Moser and Dervan, *Science* 238:645 (1987); Praseuth et al., *Proc. Natl. Acad. Sci. USA* 85:1349 (1988); Mergny et al., *Biochemistry* 30:9791 (1991); Beal and Dervan, *Science* 251:1360 (1991); Mergny et al., *Biochemistry* 30:9791 (1991) and Beal and Dervan, *Nuc. Acids Res.* 11:2773 (1992), which are incorporated by reference herein.)

A useful measure of triple helix formation is the equilibrium dissociation constant, $K_d$, of the triplex, which can be estimated as the concentration of oligonucleotide at which triplex formation is half-maximal. Preferably, the oligonucleotide has a binding affinity for the target sequence in the range of physiologic interactions. The preferred oligonucleotide has a $K_d$ less than or equal to approximately $10^{-7}$ M. Most preferably, the $K_d$ is less than or equal to $2 \times 10^{-8}$ M in order to achieve significant intracellular interactions.

A variety of methods are available to determine the $K_d$ of an oligonucleotide/target pair. In the Example which follows, the $K_d$ was estimated using a gel mobility shift assay (R. H. Durland et al., *Biochemistry* 30, 9246 (1991)). In this method, two complementary 57-mers containing the sequence corresponding to bp 157 to 213 of supFG1 were annealed to make a duplex target. The purine-rich oligonucleotide was end-labeled with $\alpha$-$[P^{32}]$-ATP and T4 polynucleotide kinase, mixed with the unlabeled complementary pyrimidine-rich 57-mer at a 1:1 ratio in Tris-EDTA buffer (TE buffer, 10 mM Tris (pH 7.4), 1 mM EDTA), incubated at 65° C. for 15 minutes and cooled to room temperature. A fixed concentration of duplex DNA ($5 \times 10^{-9}$ M) was incubated with increasing concentrations of oligonucleotides in 10 µl of 10 mM Tris (pH 7.4), 1 mM spermidine, and 20 mM $MgCl_2$ at 37° C. for 2 hours. The samples were analyzed by electrophoresis in an 8% polyacrylamide gel containing 89 mM Tris HCl, 89 mM boric acid, and 20 mM $MgCl_2$ at 5 V/cm for 15 hours, followed by autoradiography. A Phosphor-Imager (Molecular Dynamics, Sunnyvale, Calif.) was used for quantitation. The oligonucleotide concentration at which the triplex formation was half-maximal was taken as the equilibrium dissociation constant (Kd). A fixed concentration of the $P^{32}$-labeled 57 bp duplex ($5 \times 10^{-9}$ M) was incubated with increasing concentrations of each oligonucleotide as indicated, for 2 hours at 37° C. The samples were analyzed by electrophoresis in an 8% polyacrylamide gel in a buffer containing 20 mM $MgCl_2$ to maintain triplex stability, followed by autoradiography.

As described in the Examples, the triplex-forming oligonucleotides herein described can have a ribose/phosphodiester backbone, or can have a different sugar/bond than that found in DNA. For example, the oligonucleotide can contain a phosphorothioate internucleoside linkage. Such an oligonucleotide has been shown to be more stable in vivo.

The oligonucleotide can further be end capped to prevent degradation using a 3' propylamine group. Procedures for 3' or 5' capping oligonucleotides are well known in the art.

Method of Administration

Preferably, the oligonucleotides are dissolved in a physiologically-acceptable carrier, such as an aqueous solution or are incorporated within liposomes, and the carrier or liposomes are injected into the organism undergoing genetic manipulation, such as an animal requiring gene therapy or anti-viral therapeutics. The preferred route of injection in mammals is intravenous. It will be understood by those skilled in the art that oligonucleotides are taken up by cells and tissues in animals such as mice without special delivery methods, vehicles or solutions.

For in vitro research studies, a solution containing the oligonucleotides is added directly to a solution containing the DNA molecules of interest in accordance with methods well known to those skilled in the art and described in more detail in the examples below. In vivo research studies are conducted by transfecting cells with plasmid DNA and incubating the oligonucleotide in a solution such as growth media with the transfected cells for a sufficient amount of time for entry of the oligonucleotide into the cells for triplex formation. The transfected cells may be in suspension or in a monolayer attached to a solid phase, or may be cells within a tissue wherein the oligonucleotide is in the extracellular fluid.

For in vitro research studies, a solution containing the oligonucleotides is added directly to a solution containing the DNA molecules of interest in accordance with methods well known to those skilled in the art and described in more detail in the examples below.

As described above, the oligonucleotide can be made in a fashion so as to increase the stability of the oligomer under physiological conditions. Methods such as end capping and changing the sugar/linkage backbone of the oligonucleotide can be applied to the oligomers herein described to increase the serum half life of the oligonucleotide.

Methods of Use

The relevance of DNA repair and mediated recombination as gene therapy is apparent when studied in the context of human genetic diseases, for example hemophilia, cystic fibrosis, sickle cell anemia and the rare, autosomal recessive disease xeroderma pigmentosum (XP). XP is a disease that exhibits its influence worldwide, with a frequency of about 1 in 250,000 in the U.S. and Europe, and roughly 1 in 40,000 in Japan. Patients diagnosed with the disease are hypersensitive to the UV component of sunlight and less than 40% will live beyond the age of 20. This hypersensitivity manifests in numerous skin and eye lesions including cancers. XP was first described in 1874 by Hebra and Kaposi. In 1882, Kaposi named the condition "xeroderma pigmentosum", referring to its characteristic dry, pigmented skin and was the first to point out the hereditary nature of the disease, noting that two patients were siblings. XP is characterized by photosensitivity, pigmentary changes, premature skin aging and the development of malignant tumors.

Cells from XP patients are unable to correctly respond to DNA damage caused by UV light. In normal functioning cells, mutations in DNA caused by UV and other common mutagens may be removed by the nucleotide excision repair pathway (NER) in mammalian cells. Briefly, the pathway involves removing the damaged nucleotides from the double-stranded DNA, and converting the resulting single-stranded DNA back to double-strandedness via the action of DNA polymerases, using the non-damaged strand as a template, and DNA ligase.

Nucleotide excision repair is strikingly similar in *E. coli* and mammals. UV sensitivity is the result of mutations in any of the genes involved in this type of repair in humans, including XP-A through XP-I and XP-V, and in any of the uvrA, uvrB, and uvrC genes in *E. coli*. UV mimetic compounds such as psoralen, cisplatin, mitomycin-C, benzo[a]pyrene and 4-nitroquinolone oxide can affect the enzymatic action of the gene encoded repair products mentioned above.

If the target gene contains a mutation that is the cause of a genetic disorder, then the oligonucleotide is useful for mutagenic repair that may restore the DNA sequence of the target gene to normal. If the target gene is an oncogene causing unregulated proliferation, such as in a cancer cell, then the oligonucleotide is useful for causing a mutation that inactivates the gene and terminates or reduces the uncontrolled proliferation of the cell. The oligonucleotide is also a useful anti-cancer agent for activating a repressor gene that has lost its ability to repress proliferation. Furthermore, the oligonucleotide is useful as an antiviral agent when the oligonucleotide is specific for a portion of a viral genome necessary for proper proliferation or function of the virus.

The oligonucleotides herein described can be used alone or in combination with other mutagenic agents. As used herein, two agents are said to be used in combination when the two agents are co-administered, or when the two agents are administered in a fashion so that both agents are present within the cell or serum simultaneously. A preferred agent for co-administration is psoralen-linked oligonucleotides as described in PCT/US/94/07234 by Yale University.

The oligonucleotides herein described can further be used to stimulate homologous recombination of a exogenously supplied, DNA fragment, into a target region. Specifically, by activating cellular mechanisms involved in DNA synthesis, repair and recombination, the oligonucleotides herein described can be used to increase the efficiency of targeted recombination.

In targeted recombination, a triplex forming oligonucleotide is administered to a cell in combination with a separate DNA fragment which minimally contains a sequence complementary to the target region or a region adjacent to the target region, referred to herein as the recombination fragment. The recombination fragment can further contain nucleic acid sequences which are to be inserted within the target region. The co-administration of a triplex forming oligonucleotide with the fragment to be recombined increases the frequency of insertion of the fragment within the target region when compared to procedures which do not employ a triplex forming oligonucleotide. It is to be understood that the fragment to be recombined can be linked or un-linked to the triplex forming oligonucleotide. The linked fragment may range in length from 4 nucleotides to 50 nucleotides. However, the unlinked fragments have a much broader range: from 30 nucleotides to several thousand. It is preferable that the triplex forming recombinagenic oligonucleotide is at least 10 nucleotides in length. It is more preferable that the oligonucleotide be at least 20 nucleotides in length. It is still more preferable that the oligonucleotide be between 30 and 60 nucleotides in length.

The triplex-forming oligonucleotides will be further understood in view of the following non-limiting examples.

EXAMPLE 1

Targeted Mutagenesis using Non-Modified Oligonucleotides

PCT/US/07234 by Yale University, describes the use of mutagen linked, triplex forming oligonucleotides (TFOs) in site-directed mutagenesis methods (herein incorporated by reference). It has now been observed that TFOs can target mutations in vivo in the absence of a linked mutagen. Experiments were conducted that demonstrate that treatment of mammalian cells with high affinity TFOs ($K_d$ less than or equal to $2\times10^{-8}$) which bind to duplex DNA, can generate mutations in a target gene within a cell. Triplex-induced mutagenesis was also tested in repair-deficient human cells derived from patients with xeroderma pigmentosum, both group A (XPA) and XP variant (XPV), in order to elucidate the role of repair pathways in the observed mutagenesis. In complementary experiments, the ability of intermolecular triple helices to stimulate repair synthesis in human cell extracts was investigated.

Materials and Methods.

Cells. Monkey COS cells were obtained from the American Type Culture Collection, Bethesda, Md., ATCC accession number 1651°CRL, and were maintained in Dulbecco's modified Eagle medium (DMEM) supplemented with 10% fetal calf serum (Gibco/BRL, Bethesda, Md.). Other cells were obtained from the NIGMS Human Genetic Mutant Cell Repository (Camden, N.J.). XPA cells (repository no. GM04429E) are SV40-transformed fibroblasts derived from a patient with xeroderma pigmentosum, complementation group A (XP12BE). XPV cells (GM02359) are primary fibroblasts derived from a patient with the variant form of xeroderma pigmentosum (XP115LO). Normal fibroblasts (GM00637F) are SV40-transformed cells derived from an apparently normal donor. The cells were grown in MEM supplemented with 10% fetal calf serum (Gibco/BRL, Bethesda, Md.).

Cell Free Extracts. Triplex induced recombination has been demonstrated using donor fragment tethered TFOs upon transfection into monkey COS cells already carrying an episome harboring target sequence. (Chan et al., (1999) J. Biol. Chem. 274(17), 11541-11548). The present invention utilizes cell free extracts. It is preferred that the extracts are human cell free extracts, although it is understood that any type of cell free extract may be used herein, including bacteria, plant, and animal. The preparation of cell free extracts is well established in the art. Briefly, for example, cells may be lysed by sonication, electroporation, homogenization, or may be ground, or freeze-thawed. The lysates are usually concentrated and then diluted in buffer containing a cocktail of protease inhibitors, subsequently concentrated in storage buffer containing glycerol and stored at −80° C.

Oligonucleotides and vectors. Oligonucleotides were obtained from Oligos Etc.(Wilsonville, Oreg.) or were synthesized by J. Flory of the W. M. Keck Biotechnology Resource Center at Yale using materials from Glen Research (Sterling, Va.). The sequences of oligonucleotides used in this experiment include:

```
                                         (SEQ ID NO:1)
    AG10      5' AGGAAGGGGG 3'

(SEQ ID NO:2)
    AG20      5' AGGAAGGGGGGGTGGTGGG 3'

(SEQ ID NO:3)
    AG30      5' AGGAAGGGGGGGTGGTGGGGAGGGGAG 3'

(SEQ ID NO:4)
    Mix30     5' AGTCAGTCAGTCAGTCAGTCAGTCAGTCAG 3'
```

AG10 (SEQ ID NO:1), AG20 (SEQ ID NO:2), and AG30 (SEQ ID NO:3) were designed to bind as third strands in the anti-parallel triple helix motif to part or all of the 30 base pair polypurine/polypyrimidine site in supFG1 (P. A. Beal and P. B. Dervan, Science 251, 1360 (1991); A. G. Letai, M. A. Palladino, E. Fromm, V. Rizzo, J. R. Fresco, Biochemistry 27, 9108 (1988); C. Helene, Curr. Opinion Biotechnology 4, 29 (1993); H. E. Moser and P. B. Dervan, Science 238, 645 (1987); D. Praseuth, L. Perrouault, T. Le Doan, M. Chassignol, N. Thuong, C. Helene, Proc. Natl. Acad. Sci. USA 85, 1349 (1988); M. Cooney, G. Czernuszewicz, E. H. Postel, S. J. Flint, M. E. Hogan, Science 241, 456 (1988).

Vectors. SV40 shuttle vectors, pSupFG1a and pSupFG2 were derivatives of pSP189 and carried new triplex-binding sites which were engineered into the supF gene (pSP189 was obtained from Otsuka Pharmaceutical, Bethesda, Md.). The modified supF genes were constructed by inserting synthetic oligonucleotides into the XhoI to EagI sites in the original supF gene using standard techniques as described by Sambrook et al., MOLECULAR CLONING: A LABORATORY MANUAL, second edition, Cold Spring Harbor Laboratory Press, New York (1990) (which is incorporated by reference herein).

Plasmid vector pSupFG1/G144C, containing a mutated version of the supFG1 amber suppressor tRNA gene, was used as the substrate for triplex-targeted recombination. The function of this gene can be readily assayed in indicator bacteria carrying an amber stop codon in the lacZ gene, and so supFG1-144 is a useful reporter of recombination events that revert the gene to the functional sequence. The supFG1-144 gene also contains a 30-bp, G-rich site at the 3' end of the gene to which the G-rich 30-mer TFO (AG30) can bind to form a triple helix in the anti-parallel motif.

In a strategy to promote targeted recombination, a TD-TFO molecule (A-AG30) (SEQ ID NO:9) was designed in which the AG30 TFO is tethered to a donor DNA fragment homologous to a region of the supFG1-144 target gene via a mixed sequence linker. In the bi-functional A-AG30 molecule, the donor fragment, A (SEQ ID NO:8), consists of a single-strand of length 40 synthesized to be homologous to positions 121-160 of the supFG1-144 gene except at position 144, where the sequence matches that of the functional supFG1 gene.

Indicator Bacteria and Plates. The use of indicator bacteria and plates is well established within the art. Indicator bacteria are defined as bacteria for which there is an identifiable enzymatic assay, phenotypic or genotypic screen for a particular mutation or mutations. Bacteria are usually defined as "reporter" because they harbor reporter genes that generally encode some easily measurable protein. Examples of commonly used reporters are the bacterial genes that encode the enzymes chloramphenicol acetyltransferase (CAT), which acetylates the antibiotic chloramphenicol, β-galactosidase, which uses X-gal as a substrate, and β-glucuronidase, which utilizes X-glucuronide as a substrate. In the cases of β-glucuronidase and b-galactosidase, a blue color can be detected visually, or histochemically if the genes are used transgenically.

Competent bacteria are generally used to introduce DNA of interest and are well known and characterized within the art. Competent indicator bacteria are a preferred embodiment of the present invention. The term "competent" is generally defined as the state that the cells are in when capable of taking up DNA. Strains of naturally transformable bacteria do exist and can usually take up DNA late in their cell cycle, usually just before they reach stationary phase. This type of bacteria can take up DNA from the environment without special treatment. Certain strains of bacteria are also capable of being artificially manipulated into a competent state. These methods are well known within the art and include treatment with calcium ions. Electoporation may also be used to "force" DNA into the cells vial a strong electric current.

Reporter plates provide a substrate, for example as described above, recognized by the reporter gene product of interest.

Depletion of Proteins from Cell Free Extracts. It is understood that methods familiar to one of skill in the art may be utilized to deplete extracts of specific proteins. For example, immunoprecipitating proteins, using monoclonal or polyclonal antibodies directed to the protein, may be used to rid the extract of the protein. Assays, such as Western bolt analysis, may be subsequently used as a check for whether the protein was removed.

Depleted cell extracts can be re-fortified with the protein or proteins by supplementing the extracts with purified protein, immuno-precipitated protein, and/or non-depleted extracts.

Gel Shift Mobility Analysis. Third strand binding was measured using a gel mobility shift assay in which two complementary 57-mers containing the sequence corresponding to bp 157 to 213 of supFG1 were annealed to make a duplex target. The purine-rich oligonucleotide was end-labeled with $\alpha$-[$P^{32}$]-ATP and T4 polynucleotide kinase, mixed with the unlabeled complementary pyrimidine-rich 57-mer at a 1:1 ratio in TE buffer, incubated at 65° C. for 15 minutes and cooled to room temperature. A fixed concentration of duplex DNA ($5 \times 10^{-9}$ M) was incubated with increasing concentrations of oligonucleotides in 10 µl of 10 mM Tris (pH 7.4), 1 mM spermidine, and 20 mM $MgCl_2$ at 37° C. for 2 hours. The samples were analyzed by electrophoresis in an 8% polyacrylamide gel containing 89 mM Tris HCl, 89 mM boric acid, and 20 mM $MgCl_2$ at 5 V/cm for 15 hours, followed by autoradiography. A Phosphor-Imager™ (Molecular Dynamics, Sunnyvale, Calif.) was used for quantitation. The oligonucleotide concentration at which the triplex formation was half-maximal was taken as the equilibrium dissociation constant (Kd).

Mutagenesis protocol. The cells were first transfected with the SV40 vector DNA pre-mixed with cationic liposomes. Approximately $2 \times 10^6$ cells per dish (at a density of $5 \times 10^4$ per $cm^2$) were transfected by the addition to the culture medium (15 ml volume) of 5 µg of pSupFG1 DNA pre-mixed with 50 µg of cationic liposomes (DOTAP, Boehringer Mannheim, Indianapolis, Ind.). After 12 hours, the cell monolayers were washed 3 times, and fresh medium containing the selected oligonucleotide at 2 µM was added.

After 12 hours, the cells were extensively washed, and the oligonucleotides were added to the growth medium at a concentration of 2 µM. The oligonucleotides were not conjugated to any mutagen but were modified to resist nuclease-mediated degradation via incorporation of either a 3' propylamine group (Glen Research, Sterling, Va.) or phosphorothioate internucleoside linkages. Similar results were obtained with either modification.

Two days later, the vector DNA was harvested from the cells for analysis of supFG1 gene mutations. Rescue of the SV40 vector DNA and transformation of bacteria for genetic analysis of the supFG1 gene were performed as previously described (P. A. Havre and P. M. Glazer, *J. Virology* 67, 7324 (1993), C. N. Parris, D. D. Levy, J. Jessee, M. M. Seidman, *J. Mol. Biol.* 236, 491(1994)). After isolation from the mammalian cells, the vector DNA was subjected to digestion with Dpn I to restrict any vector molecules that had not been replicated in the cells, taking advantage of the differences in mammalian and bacterial methylation patterns.

Triple-helix formation. The supercoiled pSupFG1 vector DNA was incubated with the indicated oligonucleotides in extracts that were supplemented with $\alpha$-$P^{32}$-dCTP to detect induced DNA synthesis. HeLa cell-free extracts were prepared essentially as described in P. M Glazer, S. N. Sarkar, G. E. Chisholm, and W. C. Summers, *Mol. Cell. Biol.* 7, 218 (1987). Repair synthesis assays were carried out as follows. Supercoiled pSupFG1 plasmid DNA at $2 \times 10^{-9}$ M plus pUC19 DNA at $5 \times 10^{-8}$ M (as an internal control) were pre-incubated with the oligonucleotides at $1 \times 10^{-6}$ M for 2 hours at 37° C. in 10 mM Tris (pH 7.4) and 10 mM $MgCl_2$. The DNA samples were added to HeLa cell extracts containing 10-15 µg/µl protein and $\alpha$-[$P^{32}$]-dCTP, additionally supplemented as described above, and incubated for 3 hours at 30° C. The DNA was extracted with phenol/chloroform, concentrated by filtration using a Centricon 100™ filter (Amicon, Beverly, Mass.), and linearized with EcoR I. The samples were analyzed by 0.7% agarose gel electrophoresis, ethidium bromide staining, and autoradiography.

DNA sequencing. The single colonies of purified mutants were picked into 5 ml of L broth containing ampicillin (50 µg/ml) and were incubated at 37° C. for 16-20 hours by shaking at 250 rpm. Cells from 3 milliliters of culture were collected by centrifugation. Isolation of plasmid DNA was accomplished using the Wizard™ plasmid miniprep DNA purification system (Promega, Madison, Wis.). 1.5 µg of plasmid DNA was used for DNA sequencing using an ABI™ cycle-sequencing kit in accordance with the manufacturer's instructions (Applied Biosystems Inc., Foster City, Calif.) using standard methods. The sequencing primer was chosen to bind to the β-lactamase gene just upstream of the supF gene in the vector.

Results

Figure 1:
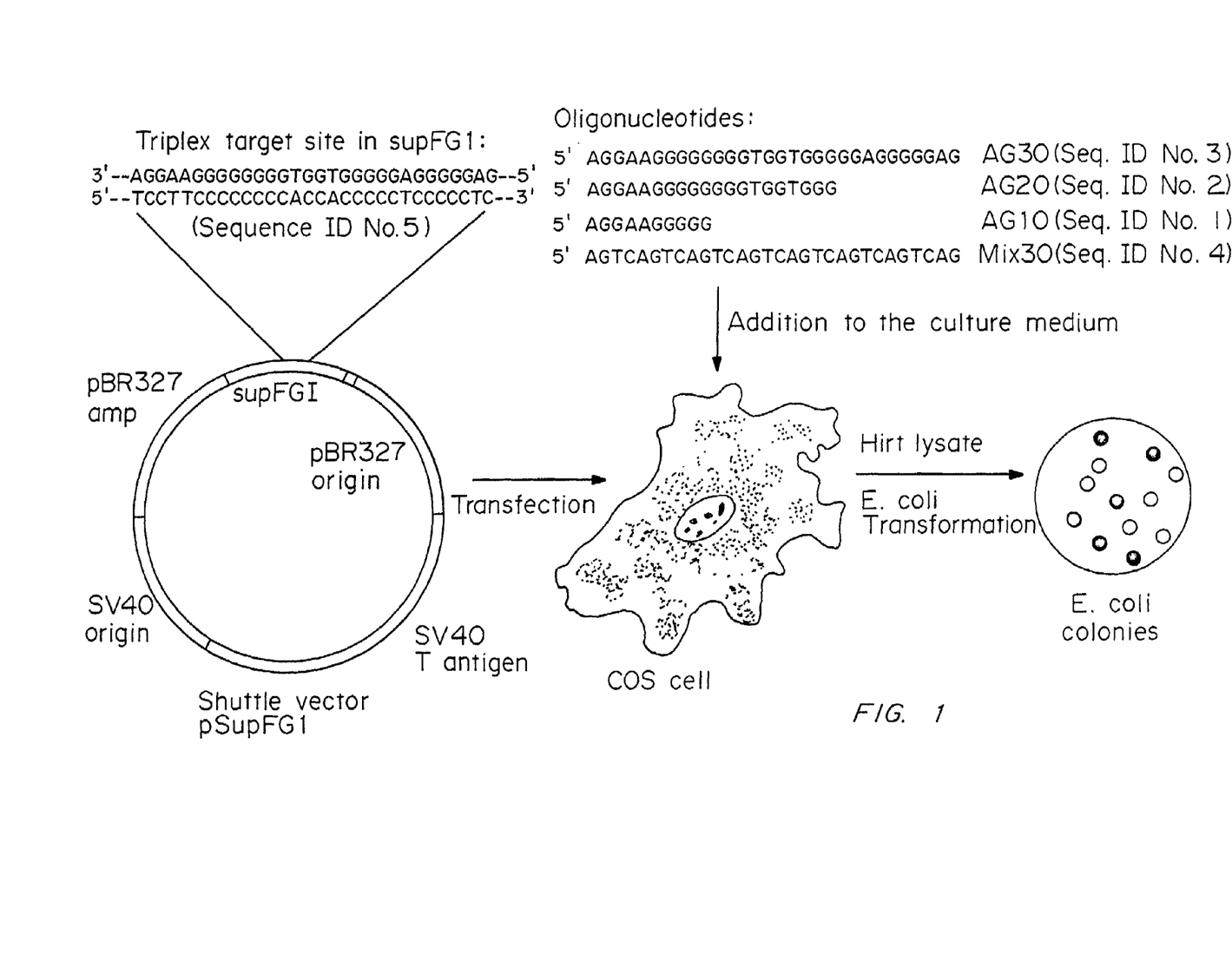
FIG. 1. Shuttle vector protocol to detect intracellular triple-helix-induced mutagenesis (SEQ ID NO:1-5).

The sequence of the selected triple helix target site in the supFG1 reporter gene within the SV40 vector is presented in FIG. 1 (SEQ ID NO:5), G. Wang, D. D. Levy, M. M. Seidman, P. M. Glazer, *Mol. Cell. Biol.* 15, 1759 (1995)), along with the sequences of the oligonucleotides studied in these experiments (SEQ ID NO:1-4).

The binding of these oligonucleotides to the triplex site in supFG1 was examined using a gel mobility shift assay (R. H. Durland et al., *Biochemistry* 30, 9246 (1991)), in which triplex formation is detected by the reduced mobility of a radioactively-labeled, synthetic 57 bp fragment matching base pairs 157-213 in the gene.

Based on the concentration-dependence of the triplex formation, the equilibrium dissociation constants (Kd) for AG10 (SEQ ID NO:1), AG20 (SEQ ID NO:2), and AG30 (SEQ ID NO:3) were determined to be approximately $3 \times 10^{-5}$ M, $3 \times 10^{-7}$ M, and $2 \times 10^{-8}$ M, respectively.

These oligonucleotides were tested for their ability to induce mutations in the pSupFG1 SV40 vector within monkey COS cells (FIG. 1, Table 1).

Oligonucleotide AG30 (SEQ ID NO:3) generated mutations in the target gene at a frequency of 0.27%, 13-fold over the spontaneous background in the assay. In contrast, AG10 (SEQ ID NO:1) and AG20 (SEQ ID NO:2), which show inferior third strand binding to supFG1, were much less effective in producing mutations. As an additional control, an oligonucleotide of 30 nucleotides in length, consisting of a mixture of all 4 bases (Mix30 (SEQ ID NO:4), FIG. 1), was also tested. It does not form a detectable triple helix with supFG1, and it did not generate any mutagenesis above the background.

TABLE 1

Mutagenesis induced by triple helix formation within monkey COS cells.

| Oligo-nucleotide | Kd for third strand binding* | Mutants/Total- | Mutation Frequency (%)- |
|---|---|---|---|
| None | — | 9/44,850 | 0.02 |
| Mix30 (SEQ ID NO:4) | No detectable binding | 5/16,590 | 0.03 |
| AG10 (SEQ ID NO:1) | $3 \times 10^{-5}$ M | 10/14,475 | 0.07 |
| AG20 (SEQ ID NO:2) | $3 \times 10^{-7}$ M | 11/10,399 | 0.11 |
| AG30 (SEQ ID NO:3) | $2 \times 10^{-8}$ M | 148/54,899 | 0.27 |

*Kd, equilibrium dissociation constant for triple helix formation.
-The values represent the frequency of mutations detected in the pSuPFG1 SV40-based shuttle vector following electroporation of the vector DNA into COS cells, subsequent treatment of the cells with the indicated oligonucleotides at a concentration of 2 µM, and rescue of the vectors for genetic analysis in bacteria 48 hours later.

Figure 2:
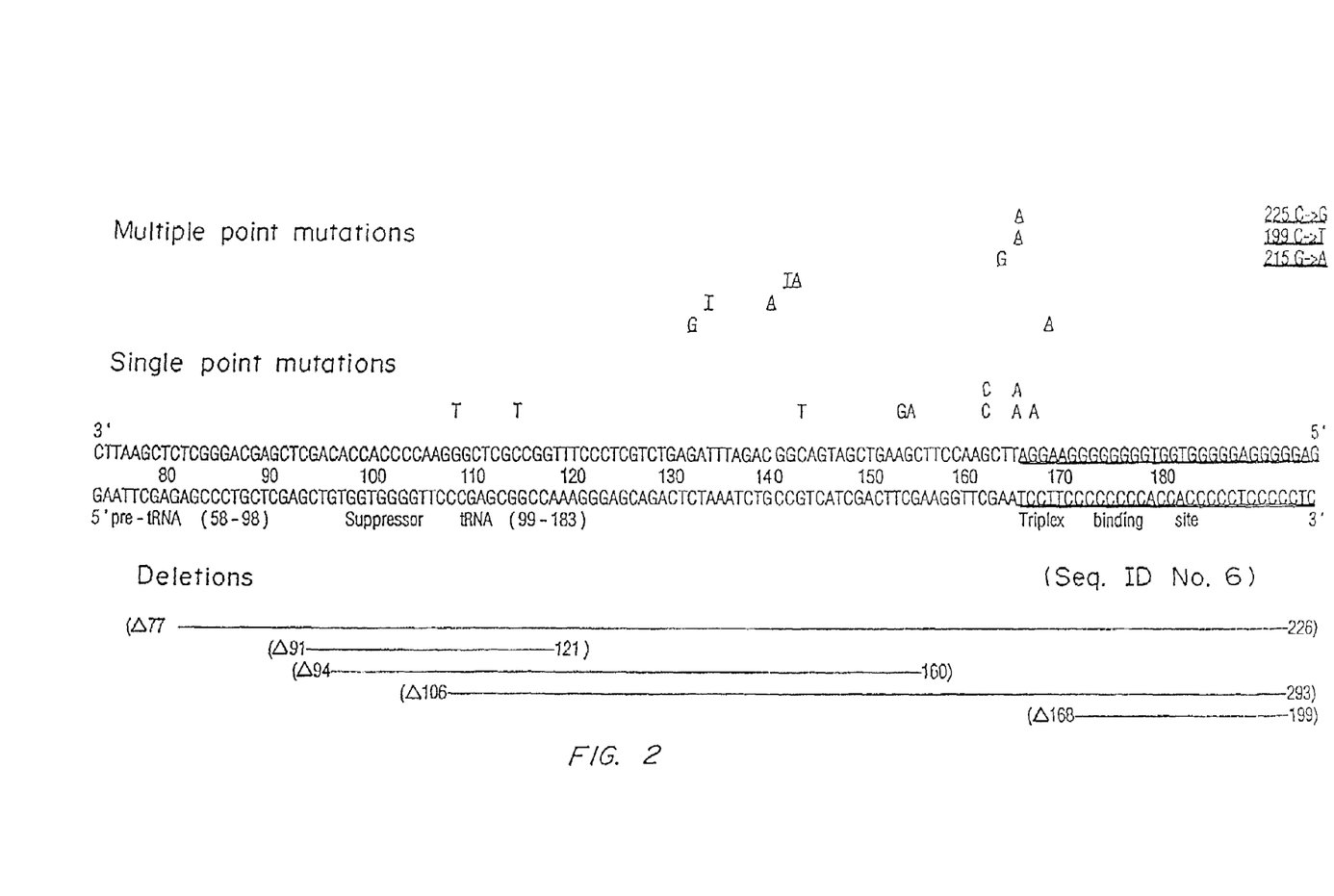
FIG. 2. Sequences of supFG1 mutations induced by triple helix formation in COS cells. (SEQ ID NO:6)

The supFG1 mutations generated by AG30 (SEQ ID NO:3) in COS cells were examined by DNA sequence analysis (FIG. 2). Sequencing of the supFG1 gene mutations was performed directly from the plasmid vector DNA using a primer complementary to a region in the b-lactamase gene adjacent to the supFG1 gene.

Mostly point mutations, along with some deletions, were seen (FIG. 2). Notable among the point mutations were several occurrences of multiple base substitutions. Three classes of mutations were observed, including single point mutations, deletions, and multiple, simultaneous point mutations, as indicated. The base substitutions listed above the corresponding supFG1 gene sequence represent changes with respect to the upper strand. The multiple point mutations are indicated by the underlining, with each set of simultaneous changes presented on a separate line. Point mutations occurring outside of the listed sequence are indicated by position numbers, with the involved base changes given. The deletions are presented below the gene sequence, with the deletion endpoints indicated.

To investigate a possible role for DNA repair in the triplex-induced mutagenesis, the ability of these TFOs to cause mutations within both repair-ski is deficient (XPA and XPV) and repair-proficient (normal fibroblasts) human cells was examined (Table 2).

In the XPA cells, which have a defect in the DNA damage recognition protein that is a component of a ternary repair endonuclease complex, no triple helix-targeted mutagenesis was seen (C. H. Park and A. Sancar, *Proc. Natl. Acad. Sci. USA* 91, 5017 (1994); C. J. Jones and R. D. Wood, *Biochemistry* 32, 12096 (1993)).

TABLE 2

Mutagenesis induced by triple helix formation in human repair-deficient and repair-proficient cell lines.

| Cell line* | Oligo-nucleotide- | Mutants/Total- | Mutation Frequency (%)- |
|---|---|---|---|
| Normal fibroblasts | None | 5/12,250 | 0.04 |
| | Mix30 | n.d. | n.d. |
| | AG30 | 50/21,575 | 0.23 |
| XPA | None | 13/48,329 | 0.03 |
| | Mix30 | 14/42,500 | 0.03 |
| | AG30 | 9/32,750 | 0.03 |
| XPV | None | 0/8,350 | <0.01 |
| | Mix30 | 4/6,895 | 0.06 |
| | AG30 | 71/8,704 | 0.82 |

*XPA, fibroblasts derived from a patient with xeroderma pigmentosum, complementation group A; XPV, fibroblasts derived from a patient with xeroderma pigmentosum variant.
-AG30 (SEQ ID NO:3) binds strongly as a third strand to the target supFG1 gene (Kd = $2 \times 10^{-8}$ M), whereas Mix30 (SEQ ID NO:4) shows no detectable binding.
-The values represent the frequency of mutations detected in the pSupFG1 SV40-based shuttle vector following electroporation of the vector DNA into the indicated cells, subsequent treatment of the cells with the indicated oligonucleotides at a concentration of 2 µM, and rescue of the vectors for genetic analysis in bacteria 48 hours later.
n.d., not determined.

The mechanism by which the triple helix formation induces mutations was further investigated by testing the ability of triple helices to stimulate repair synthesis on the vector template in HeLa cell-free extracts (R. D. Wood, P. Robins, T. Lindahl, *Cell* 53, 97 (1988), Sibghat-Ullah, I. Husain, W. Carlton, A. Sancar, *Nucleic Acids Res.* 17, 447 (1989); M. K. K. Shivji, M. K. Kenny, R. D. Wood, *Cell* 69, 367 (1992); J. T. Reardon, P. Speilmann, J. Huang, S. Sastry, A. Sancar, J. E. Hearst, *Nucleic Acids Res.* 19, 4623 (1991)).

This type of protocol has been used to study repair synthesis associated with UV and chemical damage and to isolate factors involved in nucleotide excision repair. As an internal control, pUC19 plasmid DNA (which lacks the triplex target site) was included along with pSupFG1 DNA in all samples. Following incubation in the extracts, the plasmids were linearized by digestion with EcoR I and analyzed by agarose gel electrophoresis. The DNA in each sample was visualized by ethidium bromide-staining to show that the quantities of the pSupFG1 and pUC19 DNAs were essentially constant in all the samples.

Incorporation of the labeled nucleotide into the plasmid DNA was determined by autoradiography. AG30 (SEQ ID NO:3) and, to a lesser extent, AG20 (SEQ ID NO:2), stimulated labeling of pSupFG1 but not of pUC19, consistent with high affinity, sequence-specific triplex formation by these two TFOs. Neither AG10 (SEQ ID NO:1), which binds poorly to pSupFG1 (at the 0.25 µM concentration in the extract reactions), nor Mix30, which does not bind at all, induced any repair synthesis above background. Hence, there appears to be a repair activity in the HeLa extracts that recognizes a tightly bound third stand as a lesion, leading to repair synthesis and label incorporation. Stimulation of label incorporation occurs with oligonucleotides that are substituted at the 3' end with a propylamine group, and so the argument that the oligonucleotides simply serve as primers can be ruled out.

The data presented here demonstrate that high affinity, oligonucleotide-mediated triple helix formation is mutagenic in mammalian cells, via a pathway that may involve specific repair activities.

Although significantly above background, the frequency of triplex-induced mutations reported here (in the range of 0.2 to 0.8%) is still somewhat lower than the targeted mutation frequency observed when TFOs are used to deliver a tethered psoralen molecule to a target site within cells (2.1%, See PCT/US94/07234). Since psoralen is a highly reactive mutagen upon photoactivation, it is not surprising that a triplex-targeted psoralen adduct is more effective in inducing mutations than is triple helix formation alone. However, genetic manipulation using such mutagen-conjugated TFOs requires either control over the reactivity of the mutagen (as with photoactivation) or entails the risk of non-specific reactivity of the tethered reagent. The ability of oligonucleotides without any tethered reactive group to generate mutations in a target gene overcomes these potential drawbacks. It offers the possibility of highly specific genetic manipulation using appropriately designed oligonucleotides that bind with high affinity to their target sites.

EXAMPLE 2

Triplex Induced Recombination in HeLa Cell-Free Extracts

The ability of triplex formation to promote recombination with human cell-free extracts was tested using the following procedure.

Selected oligonucleotides were incubated with the target pSupFG1/G144C vector in Hela whole cell extracts supplemented with nucleotides and ATP. Following a 2 hour incubation, the plasmid vector DNA was isolated and used to transform recA, lacZ(amber) indicator *E. coli* to score for supFG1 gene function. The bi-functional oligonucleotide A-AG30 (SEQ ID NO:9) was active in the extracts and produced supFG1-144 gene reversion at a frequency of $45 \times 10^{-5}$. This effect occurred in the extract and was not mediated by recombination in the indicator bacteria, because, without incubation in the extract, no recombinant products were observed upon transformation of the A-AG30 (SEQ ID NO:9) sample into bacteria. The A donor fragment was also somewhat active, as co-mixture of A plus the pSupFG1/G144C plasmid led to a low level of supFG1 reversion, consistent with the ability of short fragments of DNA to mediate recombination and marker rescue. (Campbell et al., 1989 *New Biol.* 1(2),223-7; Goncz and Gruenert, 2000 *Methods Mol. Biol.* 133, 85-89; Lin et al., 1987 *Mol. Cell Biol* 7(1), 129-140). However, the effect of A-AG30 was 4-fold higher than that of A alone, demonstrating the influence of the TFO domain and providing direct evidence for triplex-induced recombination in vitro. By itself, however, the TFO domain produced minimal reversion over background, indicating the need for the sequence information provided by the A donor fragment.

A sample in which AG30 (SEQ ID NO:3) and the A donor oligonucleotide (SEQ ID NO:8) were not linked but rather were simply co-mixed as separate molecules together with the plasmid substrate also produced an increased level of recombination, at a frequency of $40 \times 10^{-5}$, almost as high as that produced by the linked A-AG30 (SEQ ID NO:9). This result provides further evidence that a TFO can stimulate recombination between a donor fragment and target locus. In addition, because the donor fragment in this case is separate from the TFO, the result specifically demonstrates a role for the TFO in stimulating recombination that is distinct from its ability to deliver a tethered donor fragment to the target site.

In another sample tested, the A donor was linked to an oligonucleotide segment designated SCR30 (SEQ ID NO:7), consisting of the same base composition as AG30 (SEQ ID NO:3) but a scrambled sequence creating 12 mismatches. SCR30 (SEQ ID NO:7) does not bind to the supFG1 gene and so does not form a triplex. It has no homology to the target gene. Linkage of SCR30 (SEQ ID NO:7) to the donor fragment was found to actually inhibit recombination relative to the donor fragment alone.

EXAMPLE 3

Cell Extract Depletion and Assay

A. Using the in vitro cell extract system from Example 1 and Example 2, selected recombination and repair proteins in the pathway of triplex induced recombination were selected to determine their roles. HsRAD51 is a human RecA homolog that functions in homologous recombination and has been shown to mediate DNA pairing and strand exchange reactions. (Baumann, P. and West, S. C., 1998 *Trends Biochem Sci* 23(7), 247-251). Polyclonal rabbit anti-HsRAD51 antibody were used to deplete HsRAD51 protein from the cell extract. Successful depletion of HsRAD51 from the extract was confirmed by Western Blot. The depleted extract was tested for the ability to support triplex-induced recombination (Table 3), both in the case of the linked A-AG30 (SEQ ID NO:3) bi-functional molecule and in the case of the co-mixed separate A (SEQ ID NO:8) and AG30 (SEQ ID NO:3) sample. Immuno-depletion of HsRad51 was found to substantially reduce the frequency of recombinants in both cases. Control samples demonstrated that protein A sepharose, in the absence of the HsRad51 polyclonal antibody, had no effect.

B. Previous work studying TFO-induced mutagenesis and recombination within SV40 vectors in human cells, provided genetic evidence that the ability of triplex formation to stimulate DNA metabolism is dependent on the activity of the NER pathway. (Wang, G. et al. 1996 *Proc. Natl. Acad. Sci. USA* 93(8),3608-12; Faruqi et al., 2000 *Mol Cell Biol* 20(3), 990-1000). The requirement for the NER damage recognition factor, XPA (Sancar, A., 1996, *Annu. Rev. Biochem.* 65, 43-81), was tested in the triplex-induced recombination in the HeLa cell extracts, to obtain direct biochemical evidence in support of the proposed mechanism.

A rabbit polyclonal antibody was raised against recombinant human XPA protein produced in *E. coli* and was found to recognize the XPA protein in human cells. Using this antibody, XPA was removed from the extracts by immuno-precipitation. Depletion of XPA was confirmed by Western blot analysis of the residual samples. Depletion of XPA from the extracts was found to substantially reduce the frequency of TFO-induced recombination, whether or not the TFO was covalently linked to the donor fragment (Table 6). With both the A-AG30 (SEQ ID NO:9) and the A (SEQ ID NO:8)+AG30 (SEQ ID NO:3) samples, the depletion of XPA reduced the frequency of recombinants to that mediated by the donor fragment alone (Table 3). Hence, the ability of a triple helix to stimulate recombination depends on the XPA protein. This result supports the hypothesis that the NER pathway can recognize a triple helix as a "lesion", thereby provoking DNA metabolism that can lead to recombination or mutation.

EXAMPLE 4

Addition of Protein to Depleted Cell Extracts

A. The extent to which the triplex-induced recombination in the HsRad51-depleted extracts could be restored by the addition of purified, recombinant HsRad51 protein was tested. Increasing amounts of HsRad51 protein were added to the depleted extracts, and the recombination assay was carried out (Table 4). After the addition of a large amount of HsRAD51 (up to 5 µg), a portion of the triplex-induced recombination activity was recovered. Full complementation may not be observed because immuno-depletion of the extracts may have removed other factors physically associated with HsRad51. To test this, re-solubilized HsRad51 immuno-precipitate was used to supplement the immuno-depleted extracts (Table 4). Addition of the solubilized immunoprecipitate to the depleted extracts was found to almost completely restore the recombination activity, indicating that HsRad51 immuno-depletion removes more than HsRad51 alone and that HsRad51 supplementation, by itself, cannot compensate for the loss of the other factors. This result is not surprising in light of emerging evidence that the recombination complex in human cells consists of multiple factors, including Rad52, Rad54, XRCC2, and XRCC3, as well as members of the RAD51 family, including Rad51B/Rad51L1, Rad51C/Rad51L2, and Rad51D/Rad51L3. (Thacker, J., 1999, *Trends Genet* 15(5), 166-8; Sung, P. et al., 2000, *Mutat Res* 451(1-2), 257-75).

B. The ability of XPA to restore the triplex-induced recombination activity to XPA immuno-depleted cells was tested (Table 6). The results show that increasing amounts of XPA protein provide functional complementation in the depleted extracts. These results establish a direct role for XPA in mediating the ability of a triple helix to stimulate recombination.

EXAMPLE 5

Addition of Protein to the Complete Cell Extract

Increasing amounts of HsRad51 (from 250 ng to 2 µg) were added to non-depleted whole cell extracts, and triplex-induced recombination was measured (Table 5). Additional HsRad51 was found to increase the frequency of the triplex-induced recombinants, both in the case of the linked donor fragment and TFO (A-AG30) (SEQ ID NO:9) and the un-linked donor plus TFO (A (SEQ ID NO:8)+AG30 (SEQ ID NO:3)). There was a minimal effect in the samples supplemented with a minimal amount of HsRad51. But at higher levels of supplementation, increased yields of recombinants were seen. Hence, even though HsRad51, by itself, cannot fully complement the activity of the immuno-depleted extracts, it can provide increased activity to otherwise complete whole cell extracts.

EXAMPLE 6

Specific Mutations Induced by Triplex-Forming Oligonucleotides in Mice

Little progress has been made toward introducing mutations in somatic cells of living organisms. This example shows that TFOs can induce mutations at specific genomic sites in somatic cells of adult mice.

Mutation detection was facilitated by the use of transgenic mice bearing chromosomal copies of the supF and cII reporter genes. Mice treated with a supF-targeted TFO displayed about fivefold greater mutation frequencies in the supF gene compared with mice treated with a scrambled sequence control oligomer. No mutagenesis was detected in the control gene (cII) with either oligonucleotide. These results demonstrate that site-specific, TFO-directed genome modification can be accomplished in intact animals. By inducing site-specific mutations into the genome, heritable changes can be achieved in gene function and expression.

EXAMPLE 7

Heritable Changes in Mice as a Result of Inducing Site-Specific Mutations in the Genome Transgenic mice (C57BL/6 mice containing multiple copies of a chromosomally integrated supFG1 vector, designated 3340) were generated as described by Narayanan, et al., *Proc. Natl. Acad. Sci. USA* 94:3122 (1997) containing a 30-base pair (bp) triplex-targeted site within the supFG1 mutation reporter gene. TFO-targeted mutations in the supFG1 gene in vitro on intracellular plasmid targets and on a chromosomal locus in a fibroblast cell line established from these mice (Wang, et al., *Mol. Cell. Biol.* 15, 1759 (1995); Wang, et al., *Science* 271, 802 (1996); and Vasquez, et al., *Nucleic Acids Res.* 27, 1176 (1999)). The results revealed 10- to 100-fold induction of site-specific mutations in cells treated with the specific TFO. Although psoralen conjugation to the TFO, coupled with UVA (ultraviolet, long wave) irradiation, generally increased the frequency of mutations, targeted mutagenesis was seen even without psoralen photoproduct generation, suggesting a substantial triplex-mediated process of mutagenesis. On the basis of these results, the oligonucleotides in this work were not conjugated to psoralen, and no other DNA-damaging agent (or mutagen) was required to induce mutagenesis. This affords an advantage in that UV activation is not required, and there is no toxicity to the animals.

Mice were given daily intraperitoneal (i.p.) injections with 1 mg day$^{-1}$ of either AG30 or SCR30 for five consecutive days. AG30 is the specific TFO designed to bind to the polypurine site in the supFG1 gene, whereas SCR30 is a control oligonucleotide with the same base composition as AG30 but with a scrambled sequence that differs at 12 positions. AG30 (SEQ ID NO:3) (5'AG-GAAGGGGGGGGTGGTGGGGGAGGGGGAG-3') binds with high affinity to the 30-bp polypurine target site in the supFG1 reporter gene. SCR39 (SEQ ID NO:7) (5'GGAG-GAGTGGAGGGGAGTGAGGGGGGGGGG-3') is a control oligonucleotide with the same base composition as AG30 (SEQ ID NO:3), but a scrambled sequence (differing from AG30 (SEQ ID NO:3) at 12 positions). All oligonucleotides were synthesized with a 3' propanolamine group to prevent degradation. Using gel mobility shift assays and deoxyribonuclease I (DNase I) footprinting, AG30 (SEQ ID NO:3) binds with high affinity (equilibrium dissociation constant ~10$^{-9}$ M) and specificity to the target site, whereas SCR30 (SEQ ID NO:7), having mismatches in the triplex binding code, does not. Then days after injection, mouse tissues were collected for mutation analysis.

Transgenic mice (3340) were generated with about 15 copies of the supFG1 shuttle vector, containing the supFG1 tRNA suppressor gene, integrated on chromosome 7 (Narayanan, et al., (1997)). Mice (8 weeks of age) were injected (i.p.) with oligonucleotides for 5 days, and 10 days after the last injection, mice were killed and tissue collected. Genomic DNA was isolated from mouse tissues, and packaging extracts were used to excise and package the vector DNA into viable phage particles for analysis in a lacZ(am) strain of *Escherichia coli* to detect mutations that occurred in the mouse (Narayanan, et al., (1997). In the presence of a wild-type supFG1 gene, the amber mutation in the thiogalactopyranoside gene is suppressed and the plaques are blue, whereas the mutant plaques are white. The combined mutation frequencies in a variety of tissues from AG30 (SEQ ID NO:3)-treated mice were increased by about five-fold compared with tissues form SCR30 (SEQ ID NO:7)-treated mice (Table 7). The mean mutation frequencies in liver, skin, kidney, colon, small intestine, and lung from AG30-treated mice were significantly higher than those from SCR-30 (SEQ ID NO:7) treated mice (P values calculated by the student's t test are listed in Table 7). These data demonstrate an oligonucleotide-specific induction of mutagenesis in mice. Additionally, these data indicate efficient tissue and cell uptake and distribution of oligonucleotides in mice after i.p. injections. As a control, mutagenesis was not induced above background levels in brain tissues analyzed from mice treated with either AG30 (SEQ ID NO:3) or SCR30 (SEQ ID NO:7). In contrast, all other tissues tested from AG30 (SEQ ID NO:3)-treated animals showed an average five-fold increased induction in mutagenesis compared with tissues from SCR30-treated animals.

The levels of mutagenesis obtained from mice injected with SCR30 (SEQ ID NO:7) were similar to those observed in mice injected with phosphate-buffered saline (PBS) only, showing that SCR30 (SEQ ID NO:7), even at a dose of 1 mg per day for 5 days, does not have any detectable mutagenic effect in the animals. The values for both the SCR30- and PBS-injected animals, furthermore, were essentially the same as those observed in untreated animals in the same 3340 lineage. These results not only provide additional evidence that AG30 (SEQ ID NO:3)-mediated mutation induction is occurring through a sequence-specific, triplex-mediated mechanism, but also indicate that nonspecific oligonucleotides are not generally mutagenic in animals.

EXAMPLE 8

AG30 (SEQ ID NO:3) Treatment is Specific

To confirm that the induced mutagenesis obtained from AG30 (SEQ ID NO:3) treatment resulted from a triple-helix-dependent event and not form some hypothetical, nonspecific effect of AG30 (SEQ ID NO:3) on DNA metabolism, the effect of AG30 (SEQ ID NO:3) and SCR30 (SEQ ID NO:7) in the Mutamouse mutagenesis model (Myhr, Environ. Mol. Mutagen, 18, 308(1991)) was tested. The lambda cII gene as a mutation reporter, because this locus has been well studied (Jakubczak, et al., Proc. Natl. Acad. Sci. USA 93, 9073 (1996)) and does not contain the AG30 triplex target site. The cII control gene showed no induction of mutagenesis in animals treated with either AG30 (SEQ ID NO:3) or SCR30 (SEQ ID NO:7) compared with background levels (Table 8). These results rule out any nonspecific mutagenic effect of AG30 (SEQ ID NO:3) and are consistent with a gene-specific, triplex-mediated effect of AG30 (SEQ ID NO:3) in inducing an increased level of mutagenesis in the supFG1 gene of 3340 mice.

Mutant plaques were isolated from a variety of tissues from AG30 (SEQ ID NO:3)-treated animals, and the supFG1 genes were analyzed by DNA sequencing. These results are consistent with a TFO-directed effect with the majority (85%) of the mutations concentrated with the 30-bp triplex target site. Nearly 40% of the mutations are single-base insertions or deletions in a stretch of eight contiguous Gs. It is possible that these mutations resulted from slippage errors during TFO-induced repair, because this site has been shown previously to be prone to slippage events. Narayanan et al. 1997; Vasquez et al. 1999.

Specific TFO treatment increases the proportion of mutations at the G-rich polypurine site and also increases the absolute mutation frequency at this site more than five-fold, in a highly sequence-specific manner. Hence, the hypermutability of G-rich (or A-rich) sites is a property that actually enhances the utility of TFOs that preferentially bind to such sites in efforts directed at somatic gene knockout.

The potential of a triplex-based strategy to target mutations to a specific gene in the somatic tissues of mice is investigated here. The results demonstrate substantial induction of mutagenesis in a variety of tissues with a TFO (AG30) (SEQ ID NO:3) designed to bind to the chromosomal triplex target site in transgenic animals. No induction of mutagenesis with either AG30 (SEQ ID NO:3) or SCR30 (SEQ ID NO:7) in the supFG1 gene in brain tissue, or in the cII control gene lacking the AG30 (SEQ ID NO:3) triplex target site. Additionally, no induced mutagenesis was detected in the target gene in any of the tissues tested with the control oligonucleotide, SCR30 (SEQ ID NO:7). These findings demonstrate the successful application of a site-specific, DNA-binding reagent to specifically induce genome modifications on a chromosomal target in intact animals.

TABLE 3

Effect of HsRad51 depletion on triplex-induced recombination in cell-free extracts.

| Oligo | Extract treatment | blue colonies/ total | Reversion frequency × $10^{-5}$ |
|---|---|---|---|
| None | Standard | 0/110,000 | 0 |
| A-AG30 | No extract | 0/95,000 | 0 |
| A-AG30 | Standard | 53/99,000 | 54 |
| A-AG30 | Protein A sepharose | 45/93,000 | 48 |
| A-AG30 | HsRad51 antibody | 9/110,000 | 8 |
| A + AG30 | Standard | 42/105,000 | 40 |
| A + AG30 | Protein A sepharose | 36/96,000 | 38 |
| A + AG30 | HsRad51 antibody | 9/99,000 | 9 |

The results represent the combined data from three independent experiments. A-AG30 (SEQ ID NO:9) and A (SEQ ID NO:8) + AG30 (SEQ ID NO:3).

TABLE 4

Effect of HsRad51 supplementation on triplex-induced recombination in HsRad51-depleted cell-free extracts.

| Oligo | Extract treatment | Blue colonies/ total | Reversion frequency × $10^{-5}$ |
|---|---|---|---|
| None | Standard | 0/111,000 | 0 |
| A-AG30 | No extract | 0/99,000 | 0 |
| A-AG30 | Standard | 51/112,000 | 46 |
| A-AG30 | HsRad51 antibody | 12/112,000 | 11 |
| A-AG30 | HsRad51 antibody + 500 ng HsRad51 | 12/117,000 | 10 |
| A-AG30 | HsRad51 antibody + 1 μg HsRad51 | 15/105,000 | 14 |
| A-AG30 | HsRad51 antibody + 2 μg HsRad51 | 18/112,000 | 16 |
| A-AG30 | HsRad51 antibody + 5 μg HsRad51 | 21/114,000 | 18 |
| A-AG30 | HsRad51 antibody + 10 μl solubilized HsRad51 immuno-precipitate | 40/108,000 | 37 |
| A-AG30 | HsRad51 antibody + 20 μl solubilized HsRad51 immuno-precipitate | 46/109,000 | 42 |

TABLE 4-continued

Effect of HsRad51 supplementation on triplex-induced recombination in HsRad51-depleted cell-free extracts.

| Oligo | Extract treatment | Blue colonies/total | Reversion frequency × $10^{-5}$ |
|---|---|---|---|

The results represent the combined data from three independent experiments. A-AG30 (SEQ ID NO:9)

TABLE 5

Effect of HsRad51 supplementation on triplex-induced recombination in cell-free extracts.

| Oligo | Extract treatment | blue colonies/total | Reversion frequency × $10^{-5}$ |
|---|---|---|---|
| None | Standard | 0/93,000 | 0 |
| A-AG30 | No extract | 0/87,000 | 0 |
| A-AG30 | Standard | 54/110,000 | 49 |
| A-AG30 | plus 250 ng HsRad51 | 43/95,000 | 45 |
| A-AG30 | plus 500 ng HsRad51 | 55/98,000 | 56 |
| A-AG30 | plus 1 µg HsRad51 | 79/105,000 | 75 |
| A-AG30 | plus 2 µg HsRad51 | 103/97,000 | 106 |
| A + AG30 | No extract | 0/93,000 | 0 |
| A + AG30 | Standard | 39/105,000 | 37 |
| A + AG30 | plus 500 ng HsRad51 | 37/110,000 | 34 |
| A + AG30 | plus 1 µg HsRad51 | 54/114,000 | 47 |
| A + AG30 | plus 2 µg HsRad51 | 76/102,000 | 75 |

The results represent the combined data from three independent experiments. A-AG30 (SEQ ID NO:9) and A (SEQ ID NO:8) + AG30 (SEQ ID NO:3).

TABLE 6

Effect of XPA depletion on triplex-induced recombination in cell-free extracts.

| Oligo | Extract treatment | blue colonies/total | Reversion frequency × $10^{-5}$ |
|---|---|---|---|
| None | Standard | 0/209,000 | 0 |
| A-AG30 | No extract | 0/213,000 | 0 |
| A-AG30 | Standard | 96/219,000 | 44 |
| A-AG30 | Protein A sepharose | 45/114,000 | 39 |
| A-AG30 | XPA antibody | 18/214,000 | 8 |
| A-AG30 | XPA antibody + 75 ng XPA | 27/112,000 | 24 |
| A-AG30 | XPA antibody + 150 ng XPA | 42/114,000 | 37 |
| A-AG30 | XPA antibody + 300 ng XPA | 45/118,000 | 38 |
| A + AG30 | Standard | 46/118,000 | 39 |
| A + AG30 | Protein A sepharose | 39/111,000 | 35 |
| A + AG30 | XPA antibody | 12/115,000 | 10 |

The results represent the combined data from three independent experiments. A-AG30 (SEQ ID NO:9) and A (SEQ ID NO:8) + AG30 (SEQ ID NO:3).

TABLE 7

Targeted mutagenesis of the supFG1 gene in 3340 mice by TFOs. Mice were injected i.p. with 1 mg of TFO per day for 5 days (~50 mg kg$^{-1}$ day$^{-1}$). AG30 (SEQ ID NO: 3) is the specific TFO, SCR30 (SEQ ID NO: 7) is the control TFO. Values of mutation frequency for skin, liver, and kidney are reported as the mean ± the difference between the two values. P values were calculated by the Student's t test.

| TFO | Tissue | No. of mice | Mutants/total plaques | Mutation frequency (×$10^{-5}$) | P value |
|---|---|---|---|---|---|
| AG30 | Skin | 5 | 32/144,768 | 21 ± 10 | |
| SCR30 | Skin | 5 | 8/213,944 | 4 ± 1 | 0.006 |
| AG30 | Liver | 5 | 38/170,685 | 22 ± 7 | |
| SCR30 | Liver | 5 | 13/296,783 | 4 ± 2 | 0.0004 |
| AG30 | Kidney | 5 | 34/110,937 | 27 ± 13 | |
| SCR30 | Kidney | 5 | 12/185,818 | 6 ± 2 | 0.007 |
| AG30 | Colon | 2 | 29/76,930 | 38 ± 4 | |
| SCR30 | Colon | 2 | 8/73,275 | 11 ± 0 | |
| AG30 | Intestine | 2 | 8/18,214 | 46 ± 13 | |
| SCR30 | Intestine | 2 | 4/46,397 | 9 ± 5 | |
| AG30 | Lung | 2 | 13/56,370 | 23 ± 4 | |
| SCR30 | Lung | 2 | 4/83,190 | 5 ± 1 | |

TABLE 8

Lack of TFO-induced mutagenesis of the cII gene in Mutamice. Mice were injected i.p. with 1 mg of oligonucleotide (either AG30 (SEQ ID NO:3) or SCR30 (SEQ ID NO:7)) per day for 5 days (~50 mg kg$^{-1}$ day$^{-1}$) or with PBS.

| TFO | Tissue | No. of mice | Mutants/total plaques | Mutation frequency (×$10^{-5}$) |
|---|---|---|---|---|
| AG30 | Skin | 2 | 14/337,500 | 4 |
| SCR30 | Skin | 2 | 19/344,500 | 6 |
| None (PBS) | Skin | 2 | 16/271,000 | |

I claim:

1. A method for targeted recombination of a nucleic acid molecule to produce a change in the genome of an intact human or animal comprising the steps of:
   a) providing a single-stranded oligonucleotide having a sequence that forms a triple-stranded nucleic acid molecule by hybridizing with a target sequence in a double-stranded nucleic acid molecule with a Kd of less than or equal to $2 \times 10^{-7}$;
   b) providing a donor nucleic acid such that recombination of the donor nucleic acid into the target sequence is induced by triple helix formation between the single-stranded oligonucleotide and the double-stranded nucleic acid molecule; and
   c) administering the single-stranded oligonucleotide into an intact human or animal having a sequence that forms a triple-stranded nucleic acid molecule with the target sequence located in the genome of the intact human or animal, wherein the oligonucleotide binds to the target sequence with a Kd of less than or equal to $2 \times 10^{-7}$, and mutates the target sequence, thereby producing a change in the genome of the intact human or animal.

2. The method of claim 1 wherein the oligonucleotide is between 10 and 60 nucleotides in length.

3. The method of claim 1 wherein the oligonucleotide is dissolved in a physiologically acceptable carrier.

4. The method of claim 1 wherein the oligonucleotide is recombinagenic.

5. The method of claim 4 wherein the oligonucleotide stimulates recombination of an exogenously supplied donor nucleic acid with the target sequence of the genome.

6. The method of claim 4 wherein the oligonucleotide stimulates recombination of a donor nucleic acid that is tethered to the oligonucleotide with the target sequence of the genome.

7. The method of claim 1 wherein the target sequence is selected from the group consisting of a gene, an oncogene, a defective gene, a viral genome, and a portion of a viral genome.

8. The method of claim 7 wherein the gene is a defective-hemoglobin gene, cystic fibrosis gene, xeroderma pigmentosum gene, nucleotide excision repair pathway gene, or hemophilia gene.

9. The method of claim 1 wherein the oligonucleotide is composed of homopurine or homopyrimidine nucleotides.

10. The method of claim 1 wherein the oligonucleotide is composed of polypurine or polypyrimidine nucleotides.

* * * * *

SEQUENCE LISTING

<160> NUMBER OF SEQ ID NOS: 9

<210> SEQ ID NO 1
<211> LENGTH: 10
<212> TYPE: DNA
<213> ORGANISM: Artificial Sequence
<220> FEATURE:

<223> OTHER INFORMATION: Oligonucleotide AG10

<400> SEQUENCE: 1
aggaaggggg                                                          10

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide AG20

<400> SEQUENCE: 2
aggaaggggg gggtggtggg                                               20

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide AG30

<400> SEQUENCE: 3
aggaaggggg gggtggtggg ggaggggag                                     30

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide Mix30

<400> SEQUENCE: 4
agtcagtcag tcagtcagtc agtcagtcag                                    30

<210> SEQ ID NO 5
<211> LENGTH: 30
<212> TYPE: DNA
<213> ORGANISM: Artificial Sequence
<220> FEATURE:
<223> OTHER INFORMATION: Triplex target site in supFG1

<400> SEQUENCE: 5
tccttccccc cccaccaccc cctcccctc                                     30

<210> SEQ ID NO 6
<211> LENGTH: 124
<212> TYPE: DNA
<213> ORGANISM: Artificial Sequence
<220> FEATURE:
<223> OTHER INFORMATION: supFG1 partial sequence

<400> SEQUENCE: 6
gaattcgaga gccctgctcg agctgtggtg gggttcccga gcggccaaag ggagcagact   60
ctaaatctgc cgtcatcgac ttcgaaggtt cgaatccttc ccccccacc accccctccc  120 cctc                                                              124

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide SCR30

<400> SEQUENCE: 7

```
ggaggagtgg aggggagtga gggggggggg                                    30

<210> SEQ ID NO 8
<211> LENGTH: 40
<212> TYPE: DNA
<213> ORGANISM: Artificial Sequence
<220> FEATURE:
<223> OTHER INFORMATION: (A) donor fragment

<400> SEQUENCE: 8
agggagcaga ctctaaatct gccgtcatcg acttcgaagg                         40

<210> SEQ ID NO 9
<211> LENGTH: 77
<212> TYPE: DNA
<213> ORGANISM: Artificial Sequence
<220> FEATURE:
<223> OTHER INFORMATION: A-AG30
<220> FEATURE:
<221> NAME/KEY: misc_feature
<222> LOCATION: (41)..(41)
<223> OTHER INFORMATION: 9-atom polyethylene glycol linker
<220> FEATURE:
<221> NAME/KEY: misc_feature
<222> LOCATION: (44)..(44)
<223> OTHER INFORMATION: 9-atom polyethylene glycol linker
<220> FEATURE:
<221> NAME/KEY: misc_feature
<222> LOCATION: (47)..(47)
<223> OTHER INFORMATION: 9-atom polyethylene glycol linker

<400> SEQUENCE: 9
agggagcaga ctctaaatct gccgtcatcg acttcgaagg nttnttnagg aagggggggg   60
tggtggggga gggggag                                                  77
```